United States Patent [19]

Castelijns et al.

[11] Patent Number: 5,616,804
[45] Date of Patent: Apr. 1, 1997

[54] PROCESS FOR THE PREPARATION OF DIBENZYLAMINE

[75] Inventors: Anna M. C. F. Castelijns, Beek; Peter J. D. Maas, Schinnen, both of Netherlands

[73] Assignee: DSM N.V., Heerlen, Netherlands

[21] Appl. No.: 560,510

[22] Filed: Nov. 17, 1995

Related U.S. Application Data

[63] Continuation of Ser. No. 309,029, Sep. 20, 1994, abandoned.

[30] Foreign Application Priority Data

Sep. 20, 1993 [BE] Belgium ............................... 09300975

[51] Int. Cl.⁶ .................................................. C07C 209/78
[52] U.S. Cl. ............................................. 564/398; 564/373
[58] Field of Search ..................................... 564/373, 398, 564/396

[56] References Cited

U.S. PATENT DOCUMENTS 3,597,438  8/1971  Brake ................................ 260/296 R
4,163,025  7/1979  Plunkett et al. ..................... 260/570.9
5,266,730  11/1993  Abe et al. ............................... 564/398

FOREIGN PATENT DOCUMENTS 9313047  7/1993  WIPO.

OTHER PUBLICATIONS

Knoop & Osterlin, 'Synthesis and Degradation of Amino Acids', Z. Physiol. Chem., 170, 186–211 (1927).

Primary Examiner—Brian M. Burn
Attorney, Agent, or Firm—Cushman Darby & Cushman IP Group of Pillsbury Madison & Sutro, LLP

[57] ABSTRACT

The present process involves preparing dibenzylamine through the hydrogenation of benzaldehyde in the presence of ammonia and a catalyst containing palladium using a small amount of solvent or dispersion medium. With the present process, dibenzylamine can be prepared with high selectivity in a relatively short reaction time and with complete conversion of the benzaldehyde, at which makes it commercially attractive. In the present process, a palladium-carbon catalyst is preferably used.

12 Claims, No Drawings

1

PROCESS FOR THE PREPARATION OF DIBENZYLAMINE

This is a continuation of application Ser. No. 08/309,029, filed on Sep. 20, 1994 (now abandoned).

FIELD OF THE INVENTION

The present invention relates to a process for preparation of dibenzylamine through the hydrogenation of benzaldehyde in the presence of ammonia and a catalyst containing palladium.

BACKGROUND OF THE INVENTION

A process for preparing dibenzyl amine is described in WO-A-9313047. In this process the reaction is carried out in a homogenous solution of benzaldehyde in methanol. In order to safeguard the homogeneneity of the solution, relatively large amounts of solvents (850 wt % methanol calculated with respect to benzaldehyde) are used, which leads to a commercially less attractive process in view of low production capacities and high distillation costs. A relatively large amount of catalyst is also used, such as 2 wt. % calculated with respect to benzaldehyde.

SUMMARY AND OBJECTS OF THE PRESENT INVENTION

An object of the present invention is to overcome the above-mentioned disadvantages.

Another object of the present process is to produce dibenzylamine with a high selectivity (>90%).

A yet further object of the present process is to enable complete conversion of the benzaldehyde whereby a particularly attractive commercial process is provided.

These and other objects are accomplished by conducting the reaction in the presence of 3–60 wt. %, calculated with respect to benzaldehyde, of a solvent or dispersion medium.

DETAILED DESCRIPTION OF THE INVENTION

The present process for preparing dibenzylamine involves hydrogenating benzaldehyde in the presence of ammonia and a catalyst containing palladium and in the presence of a solvent or dispersion medium in an amount of 3 to 60 wt. %, relative to benzaldehyde.

It was discovered that, when using small amounts of solvent, a two-phase system, consisting of an aqueous phase (containing the catalyst as a solid) and an organic phase, is formed at least at the end of the reaction. In addition, it was discovered that the reaction can be carried out with very small amounts of solvent, such as less than 40 wt. % calculated with respect to benzaldehyde, so that high production capacities can be achieved. Moreover, a simple recovery procedure can be accomplished.

Exemplary solvents are lower alcohols, of which methanol and ethanol are representative. Furthermore, it was discovered that the reaction can be carried out without a separate solvent being used. In this latter embodiment, only a dispersion medium is present in the reaction mixture. The reaction then takes place in a two-phase system from the beginning.

In principle, the dispersion medium can be any liquid which is not completely miscible with benzaldehyde or dibenzylamine. By preference, the dispersion medium is water. Advantageously, with water as the dispersion medium, at the end of the hydrogenation, a 2-phase system is obtained in which almost all the dibenzylamine formed is present in the organic phase. The aqueous phase, in which the catalyst is included and in which virtually no dibenzylamine or other organic components are present, can then, if required, be recirculated as such. After recovering the catalyst, the residual aqueous phase can, if desired, be readily removed, e.g., disposed, without causing any great environmental damage.

Small amounts of solvent or dispersion medium are quite adequate to enable the reaction to run properly and to counter substantial deactivation of the catalyst. An increase in production capacity is achieved because only small amounts of solvent or dispersion medium are necessary. In principle, the quantity of solvent or dispersion medium necessary to disperse the catalyst in the reaction mixture is quite adequate. In practice, this means that the quantity of solvent or dispersion medium is in excess of 3 wt. %, calculated with respect to the amount of benzaldehyde, although the amount used is preferably about 4 to 40 wt. %, and in particular the amount used is about 5 to 20 wt. %.

The benzaldehyde used and the dibenzylamine obtained can optionally be substituted in the nucleus such as, for example, by one or more halogens, alkyl groups having 1–4 carbon atoms, or alkoxy groups having 1–4 carbon atoms.

The temperature at which the reaction is conducted can vary across a wide range. In general, the temperature ranges between about 60° C. and 150° C., and in particular ranges between about 70° C. and 130° C. The reaction is preferably carried out at a temperature between about 80° C. and 120° C. because a higher selectivity can then be achieved.

The pressure at which the reaction is carried out is not critical, and generally ranges between the vapour pressure of the reaction mixture, which is determined largely by the vapour pressure of $NH_3$ at the reaction temperature, and 20 MPa, and more particularly it ranges between about 2 and 10 MPa.

The molar ratio of $NH_3$ to benzaldehyde which is used is generally greater than 0.4. Surprisingly, the upper limit was not found to be critical. In practice, the molar ratio of $NH_3$ to benzaldehyde will generally range between about 0.5 and 1.0, and preferably is between about 0.55 and 0.7. The ratio desired is determined by the extent to which benzylamine and tribenzylamine are obtained as by-product and depends on the type of palladium catalyst. Somewhat more tribenzylamine is formed at a lower $NH_3$-benzaldehyde ratios. At a higher $NH_3$-benzaldehyde ratio, somewhat more benzylamine is formed. A useful molar ratio of $NH_3$ to benzaldehyde for a given catalyst is easily established by empirical methods.

The reaction is conducted in the presence of a catalyst. A catalyst containing palladium can be used. By preference a palladium-carbon catalyst is used. The amount of palladium with respect to carbon is generally about 5 to 10 wt. % calculated with respect to the total amount of palladium and carbon. In practice, starting from a catalyst containing 5 wt. % palladium, in most circumstances an amount of catalyst in the range of 0.05–0.2 wt. % calculated with respect to the amount of benzaldehyde will be sufficient to obtain good results. If a catalyst with a different palladium-carbon weight ratio is used, an equivalent amount of catalyst will be used. An optimal amount of catalyst is readily determined by means known to those skilled in the art.

The invention will be explained on the basis of the following non-limiting examples.

EXAMPLE I

Into an inertised reactor with a capacity of 150 ml provided with a turbine agitator were successively introduced 41.9 g benzaldehyde (395.3 mmol), 20.1 g $CH_3OH$, 0.08 g 5% palladium/carbon (Degussa; E10 R/W 50% $H_2O$ w/w) and 3.8g $NH_3$ (223.5 mmol). The reactor was then pressurized to 70 bar with hydrogen. Next, the temperature was raised to 110° C. and the pressure in the reactor increased to 85 bar with hydrogen. After approximately 15 minutes no further hydrogen was absorbed. The reactor contents were cooled to room temperature and the reactor was then depressurized and flushed with $N_2$. After the catalyst had been filtered off, the reaction mixture was found to be a 2-phase system. This 2-phase system was homogenized after the addition of the $CH_3OH$ which was used for flushing of the autoclave. The homogenous reaction mixture obtained in this way was analyzed by means of gas chromatography. All the benzaldehyde had been completely converted. The selectivity to dibenzylamine was 95.1%. In addition, small amounts of benzylalcohol (sel. approx. 1.8%) and tribenzylamine were formed.

EXAMPLES II–IX

Examples II–IX were carried out in the same manner as Example I. The results are reported in Table 1.

ized with five bar hydrogen and preheated to 60° C. Next, 4.34 kg $NH_3$ (0.255 kmol) was added, after which the temperature was increased to 90° C. and the pressure in the reactor was raised to 80 bar using hydrogen. After 45 minutes no further $H_2$ adsorption took place. The reaction was then continued for a further 30 minutes, after which the reactor contents were cooled (approximately 40° C.) and the reactor was depressurized and purged with $N_2$.

The catalyst was filtered off. After the catalyst had been filtered off, the reaction mixture was found to be a 2-phase system. After the separation of the two liquid phases the organic phase was analyzed by means of gas chromatography. All benzaldehyde had been completely converted. The selectivity of dibenzylamine was to 91.4%. In addition, small amounts of benzylalcohol (sel. approx. 0.6%), benzylamine (sel. approx. 0.5%), dibenzylamine (sel. approx. 0.1%) and tribenzylamine (sel. approx. 3.7%) were formed.

EXAMPLE XI

Into an inertised Buss loop reactor with a capacity of 50 liters were successively introduced 40.74 kg BALD (0.384 kmol) and 4.1 kg $H_2O$. The circulation pump was then started and 0.0815 kg 4% palladium/carbon (Degussa E196 NN-W; 50% $H_2O$) was added. The trial was further carried out along the same lines as Example X, except that 4.76 kg

TABLE 1

| VB | reactants (g) BALD | cat wet | moist. % | $NH_3$ | BALD $CH_3OH$ (w/w) | BALD/ $H_2O$ (w/w) | $NH_3$/ BALD (mol/ mol) | press bar | temp °C. |
|---|---|---|---|---|---|---|---|---|---|
| II | 40 | 0.8 | 50 | 13.3 | 2.0 | — | 2.3 | 85 | 100 |
| III | 50.2 | 0.1 | 50 | 6.2 | 5.0 | — | 0.77 | 85 | 110 |
| IV | 49.9 | 0.1 | 50 | 6.8 | 4.75 | — | 0.85 | 85 | 110 |
| V | 40.1 | 0.08 | 50 | 4.3 | 2.0 | — | 0.67 | 85 | 110 |
| VI | 50.1 | 0.10 | 50 | 5.7 | — | 5.0 | 0.71 | 85 | 110 |
| VII | 50.1 | 0.1 | 50 | 4.9 | — | 5.0 | 0.61 | 85 | 90 |
| VIII | 50.0 | 0.1 | 50 | 6.9 | 5.0 | — | 0.86 | 80 | 110 |
| IX | 50.2 | 0.1 | 50 | 5.5 | 5.0 | — | 0.68 | 80 | 110 |

| VB | rcat. time (min.) | conv (%) | (%) sel. BAM | BALC | DI- BAM | DI- BIM | TRI- BAM | cat. type |
|---|---|---|---|---|---|---|---|---|
| II | 10 | 100 | 1.0 | 7.6 | 91.3 | 0 | 0 | Degussa; E10 R/W |
| III | 14 | 100 | 1.7 | 0.3 | 95.6 | 0.3 | 2.3 | Degussa; E10 R/W |
| IV | 34 | 100 | 2.6 | 0.3 | 95.6 | 0.4 | 1.6 | Degussa; E103 NN/W |
| V | 10 | 100 | 0.2 | 0.5 | 97.2 | 0.2 | 2.1 | Degussa; E196 NN/W |
| VI | 20 | 100 | 0 | 1.2 | 90.4 | 0.7 | 3.7 | Degussa; E196 NN-W |
| VII | 30 | 100 | 0 | 1.5 | 92.9 | 3.3 | 4.0 | Degussa; E196 NN-W |
| VIII | 28 | 99.8 | 1.8 | 0.7 | 92.8 | 3.2 | 0.4 | Degussa; E196 NN-W |
| IX | 20 | 99.9 | 0.1 | 0.5 | 96.6 | 0.3 | 1.5 | Degussa; E196 NN-W |

EXAMPLE X

Into an inertised Buss loop reactor with a capacity of 50 liters were successively introduced 37.22 kg BLAD (0.35 kmol) and 7.51 kg $H_2O$. Next, the circulation pump was started and 0.0744 kg 5% palladium/carbon (Degussa E196 NN-WW; 50% $H_2O$) was added. The reactor was pressur- $NH_3$ (0.280 kmol) was added. Gas chromatography analysis of the organic phase showed that all the benzaldehyde had been converted. The selectivity to dibenzylamine was 92.5%. In addition, small amounts of benzylalcohol (sel. approx. 0.4%), benzylamine (sel. approx. 0.9%), dibenzylimine (sel. approx. 0–1%) and tribenzylamine (sel. approx. 2.4%) were formed.

EXAMPLE XII

Into an intertised Buss-loop reactor with a capacity of 50 liters were successively introduced 42 kg BLAD (0.396 kmol) and 3 kg $H_2O$. The circulation pump was then started and 0.084 kg 5% Pd/C (Degussa E196 NN-W; 50% $H_2O$) was added.

The reactor was pressurized to five bar with hydrogen and preheated to 60° C. Next, 49 kg $NH_3$ (0.288 kmol) was added, after which the temperature was increased to 90° C. and the pressure was raised to 80 bar with hydrogen. The Example was further carried out along the same lines as Example X. After separation of the two liquid phases, 28.3 kg of an organic phase and 11.6 kg of a water phase were obtained. Analysis of both phases gave the following compositions:

|  | Organic phase (wt. %) | $H_2O$-phase (wt. %) |
|---|---|---|
| Benzaldehyde | 0 | 0 |
| Benzylalcohol | 1.5 | 0.2 |
| Benzylamine | 1.7 | 0.5 |
| Dibenzylamine | 94.5 | 0.1 |
| Dibenzylimine | 0.3 | — |
| Tribenzylamine | 1.0 | — |
| $H_2O$ | 0.9 | — |
| $NH_3$ | 0.05 | 11.3 |

As seen from the data, all the benzaldehyde had been converted and practically no dibenzylamine was present in the waterphase. The yield of dibenzylamine ("DIBAM"), based on the amount presented in the organic phase, was 92.5%.

What is claimed is:

1. A process for the preparation of dibenzylamine comprising the step of hydrogenating benzaldehyde in the presence of ammonia and a catalyst containing palladium wherein the hydrogenation is performed in the presence of a solvent or dispersion medium in an amount of about 3 to 60 wt. % calculated with respect to benzaldehyde.

2. A process according to claim 1, wherein the solvent or dispersion medium is present in an amount of about 5 to 20 wt. %.

3. A process according to claim 1 or 2, wherein the catalyst is a palladium-carbon catalyst.

4. A process according to claim 1, wherein the dispersion medium is water.

5. A process according to claim 1, wherein the hydrogenation is carried out at a temperature between 80° C. and 120° C.

6. A process according to claim 1, 2 or 5, wherein the relative molar ratio of the ammonia and benzaldehyde reactants ranges between about 0.5 and 1.0.

7. A process according to claim 1, 2 or 5, wherein the relative molar ratio of the ammonia and benzaldehyde reactants ranges between about 0.55 and 0.7.

8. A process according to claim 1, 2 or 5, wherein the relative molar ratio of the ammonia and benzaldehyde reactants ranges between about 0.5 and 1.0 and said reaction is conducted at a temperature ranging between about 80° C. and 120° C.

9. A process according to claim 1 or 2, wherein the relative molar ratio of the ammonia and benzaldehyde reactants ranges between about 0.55 and 0.7 and said reaction is conducted at a temperature ranging between about 80° C. and 120° C.

10. A process for the preparation of dibenzylamine comprising the steps of hydrogenating benzaldehyde in the presence of a palladium-carbon catalyst and ammonia in 3 to 60 wt. % water relative to the benzaldehyde, wherein said hydrogenating is effected at a temperature of 80° C. to 120° C., the molar ratio of ammonia to benzaldehyde is between 0.5 and 1.0, and at least by the end of said hydrogenation a two-phase system is obtained.

11. A process according to claim 10, wherein the hydrogenation is conducted in 5–20 wt. % water.

12. A process according to claim 10, wherein the molar ratio of ammonia to benzaldehyde is between 0.55 and 0.7.

* * * * *